United States Patent
Hommeltoft et al.

(10) Patent No.: US 9,193,650 B1
(45) Date of Patent: Nov. 24, 2015

(54) LONG CHAIN SECONDARY ALCOHOLS FROM FATTY ACIDS AND FATTY OILS

(71) Applicants: Sven Ivar Hommeltoft, Pleasant Hill, CA (US); Cedrick Mahieux, Benicia, CA (US)

(72) Inventors: Sven Ivar Hommeltoft, Pleasant Hill, CA (US); Cedrick Mahieux, Benicia, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 14/540,420

(22) Filed: Nov. 13, 2014

(51) Int. Cl.
| | | |
|---|---|---|
| *C07C 29/00* | (2006.01) | |
| *C07C 45/48* | (2006.01) | |
| *C07C 29/145* | (2006.01) | |

(52) U.S. Cl.
CPC .............. *C07C 29/145* (2013.01); *C07C 45/48* (2013.01)

(58) Field of Classification Search
CPC ...... C07C 29/143; C07C 29/145; C07C 45/48
USPC ................................................ 568/397, 881
See application file for complete search history.

(56) References Cited

U.S. PATENT DOCUMENTS

| 4,087,398 A | 5/1978 | Heyden et al. |
| 4,808,323 A | 2/1989 | Fisher et al. |
| 5,451,701 A | 9/1995 | Zajacek et al. |
| 7,074,972 B2 | 7/2006 | Maas et al. |
| 7,479,576 B1 | 1/2009 | Hassan et al. |
| 8,519,206 B2 | 8/2013 | Holtzapple et al. |
| 8,715,486 B2 | 5/2014 | Myllyoja et al. |
| 2012/0316093 A1 | 12/2012 | Zhan et al. |

OTHER PUBLICATIONS

Khanna et al. Chemical constituents of the roots of Selinum vaginatum. Indian Perfumer, 1975, vol. 18, Pt. 2, 34-35; HCAPLUS Abstract, Accession No. 1977:490575; Document No. 87:90575.*

* cited by examiner

*Primary Examiner* — Sikarl Witherspoon
(74) *Attorney, Agent, or Firm* — Susan M. Abernathy

(57) ABSTRACT

Processes for producing long chain secondary alcohols from fatty acids and fatty oils, wherein at least one fatty acid or a fatty acid mixture is contacted with a ketonization catalyst in a ketonization catalyst under ketonization conditions to provide a long chain ketone, and the long chain ketone is contacted with a selective ketone hydrogenation catalyst that lacks catalytic activity for alcohol dehydration to selectively hydrogenate the long chain ketone to provide the corresponding long chain secondary alcohol.

19 Claims, No Drawings

LONG CHAIN SECONDARY ALCOHOLS FROM FATTY ACIDS AND FATTY OILS

TECHNICAL FIELD

This disclosure relates to processes for producing long chain secondary alcohols from fatty acids and fatty oils and to long chain secondary alcohol products.

BACKGROUND

Heretofore, long chain alcohols have typically been prepared by hydrogenation of fatty oils and fatty acids or through Fischer-Tropsch (F-T) type chemistry, both of which place the alcohol group towards the end of the molecule. Also regarding chain length, it is typically expensive to prepare alcohols with a carbon chain length above that of available fatty acids, i.e., typically up to $C_{18}$ for the most common fatty acids and fatty oil feedstocks.

There is a need for processes for efficiently producing long chain secondary alcohols from fatty acids and fatty oils.

SUMMARY

In an embodiment there is provided a process comprising contacting at least one fatty acid with a ketonization catalyst in a ketonization zone under ketonization conditions to provide at least one long chain ketone according to the following Scheme 1:

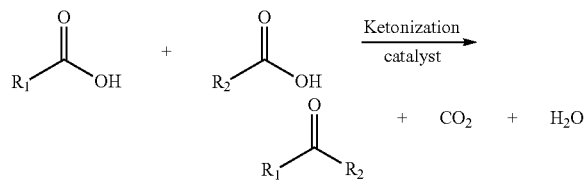

wherein $R_1$ and $R_2$ are independently selected from the group consisting of $C_5$-$C_{21}$ linear or branched alkyl and $C_5$-$C_{21}$ linear or branched alkenyl, and contacting the at least one long chain ketone with a selective ketone hydrogenation catalyst in a ketone hydrogenation zone in the presence of hydrogen gas under selective ketone hydrogenation conditions to provide at least one long chain secondary alcohol according to the following Scheme 2:

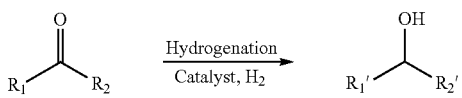

wherein $R_1$ and $R_2$ are the same or different; when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, $R_2$ and $R_2'$ have an equal number of carbon atoms, and the step of contacting the at least one long chain ketone with the selective ketone hydrogenation catalyst comprises selectively hydrogenating the at least one long chain ketone to selectively provide the at least one long chain secondary alcohol.

In another embodiment, there is provided at least one long chain secondary alcohol product, or a product comprising a mixture of long chain secondary alcohols, prepared by processes as disclosed herein.

In a further embodiment there is provided a process comprising contacting at least one fatty acid with a ketonization catalyst in a ketonization zone under ketonization conditions to provide at least one long chain ketone having at least 11 carbon atoms according to the following Scheme 1:

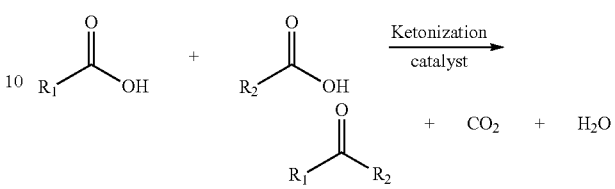

wherein $R_1$ and $R_2$ are independently selected from the group consisting of $C_5$-$C_{21}$ linear or branched alkyl and $C_5$-$C_{21}$ linear or branched alkenyl, and contacting the at least one long chain ketone with a selective ketone hydrogenation catalyst in a ketone hydrogenation zone in the presence of hydrogen gas under selective ketone hydrogenation conditions to provide at least one long chain secondary alcohol according to the following Scheme 2:

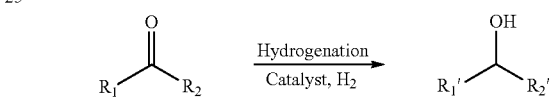

wherein $R_1$ and $R_2$ are the same or different, when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, $R_1$ and $R_1'$ have an equal number of carbon atoms, and $R_2$ and $R_2'$ have an equal number of carbon atoms. The selective ketone hydrogenation catalyst lacks catalytic activity for dehydration of the long chain secondary alcohol under said selective ketone hydrogenation conditions such that ketone conversion to the corresponding alkene or alkane is prevented, and the step of contacting the at least one long chain ketone with the selective ketone hydrogenation catalyst comprises selectively hydrogenating the at least one ketone to selectively provide the at least one long chain secondary alcohol.

In yet another embodiment there is provided a process comprising i) reacting a first fatty acid with a second fatty acid to form a long chain ketone having at least 11 carbon atoms, and ii) selectively hydrogenating the long chain ketone to selectively form the corresponding long chain secondary alcohol, wherein i) and ii) are jointly performed according to the following Scheme 3:

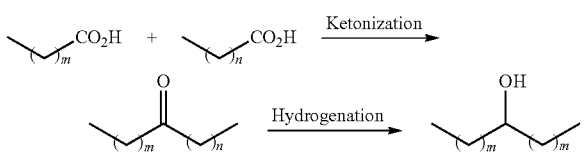

wherein each of m and n is an integer in the range from 4 to 20, and wherein m and n may be equal or unequal such that the first fatty acid and the second fatty acid may be the same or different. The step of reacting the first fatty acid with the second fatty acid comprises contacting the first fatty acid and the second fatty acid with a ketonization catalyst in a ketonization zone under ketonization conditions. The step of selectively hydrogenating the long chain ketone comprises contacting the long chain ketone with a selective ketone hydrogenation catalyst in a ketone hydrogenation zone in the presence of hydrogen gas under selective ketone hydrogenation conditions, and the step of selectively hydrogenating the long chain ketone is performed in the absence of a material that promotes dehydration of the secondary alcohol under said selective ketone hydrogenation conditions such that conversion to the corresponding alkene or alkane is prevented.

DETAILED DESCRIPTION

Conventional processes for preparing alcohols with a carbon chain length above that of available fatty acids are expensive. Also, such conventional processes place the alcohol group toward the end of the molecule.

For some applications it may be desirable to make inexpensive long chain alcohols in which the alcohol group is placed away from the termini of the molecule. Such a non-terminal location of the alcohol group ensures a lower melting point and thus better cold flow properties of derivatives of these alcohols, which is an important consideration, for example, if the alcohols are to be used for preparing products for lubricant applications.

Also for lubricant applications, it may be important to prepare molecules with a sufficiently high boiling point and viscosity to meet specifications for most lubricant products. This typically requires carbon chains considerably longer than the $C_{16}$-$C_{18}$ chains that are made simply by hydrogenation of the most commonly available fatty acids and fatty oil feedstocks.

Applicant has discovered a new route to make long chain secondary alcohols, from fatty acids and fatty oils, in which the OH group may be placed non-terminally in the molecule and in which the carbon chain length is about twice (2×) the length of the carbon chain of alcohols prepared by simple hydrogenation of fatty acids and fatty oils.

More specifically, Applicant has demonstrated that under the right conditions of temperature and pressure and in the presence of alumina catalyst, it is possible to perform fatty acid ketonization with concomitant loss of $CO_2$ and $H_2O$ to give a heavy or long chain ketone. Subsequent reduction of the long chain ketone generates long chain secondary alcohols wherein the OH group is disposed non-terminally in the molecule.

Ketone reduction to provide long chain alcohols may be performed by chemical means using reducing agents such as $LiAlH_4$. However, chemical reduction of the ketone is expensive, and in addition we have found the reactivity of the ketones towards usually very effective reducing agents such as $LiAlH_4$ decreases with increasing hydrocarbon chain length making the chemical reagents even more expensive to use. Furthermore, hydrogenation of long chain ketones over a conventional alumina supported or silica-alumina supported hydrotreating catalyst, e.g. a catalyst of the Co—Mo or Ni—Mo types, results in considerable formation of the corresponding alkanes, with concomitant decrease in yield of the desired long chain secondary alcohol product.

Applicant has further discovered that such alkane formation results from alcohol dehydration catalyzed by alumina present in the support material of conventional catalysts, i.e., the alumina in conventional catalysts dehydrates the initially formed alcohol to give an olefin that is more easily hydrogenated than the long chain ketone. Consequently, long chain ketones tend to be reduced all the way to the corresponding alkane in the presence of an alumina-supported hydrogenation catalyst.

In an embodiment, long chain secondary alcohols may be prepared by ketonization of at least one fatty acid to provide a long chain ketone, and thereafter the long chain ketone may be selectively hydrogenated to the corresponding secondary alcohol with excellent selectivity using a selective ketone hydrogenation catalyst that at least substantially lacks catalytic activity for alcohol dehydration under the hydrogenation conditions used. Such selective ketone hydrogenation allows ketone conversion to the corresponding secondary alcohol at high selectivity (e.g., >80% selectivity) at 90% conversion. While not being bound by theory, conversion of the long chain ketone to products other than the corresponding secondary alcohol may be accounted for, at least in large part, by non-catalytic (e.g., thermal) alcohol dehydration. In long chain secondary alcohols prepared in this manner, the alcohol group may be placed at a non-terminal location of the molecule. As a non-limiting example, the hydroxyl group may be located at least six carbon atoms from a terminal carbon atom of the molecule, and often in the range from 6 to 21 carbon atoms from a terminal carbon atom of the molecule.

Catalysts for Ketonization

In an embodiment, a suitable catalyst for ketonization may comprise alumina. In an embodiment, the ketonization catalyst may comprise at least 95 wt %, at least 99 wt %, or at least 99.5 wt % alumina. In an embodiment, the fresh ketonization catalyst may be calcined at a temperature in the range from 700 to 1100° F. (371 to 593° C.) for a time period in the range from 0.5 to 24 hours prior to contacting the ketonization catalyst with a reactant (long chain carboxylic acid or fatty acid). In an embodiment, the fresh ketonization catalyst may be calcined in the presence of steam. In an embodiment, the ketonization catalyst may comprise gamma alumina. In an embodiment, the ketonization catalyst may consist essentially of alumina.

In an embodiment, the surface area of the alumina catalyst for ketonization may be in the range from 15 to 500 $m^2/g$ of catalyst, or from 50 to 400 $m^2/g$ of catalyst, or from 100 to 250 $m^2/g$ of catalyst. In an embodiment, an alumina catalyst useful for ketonization reactions as disclosed herein may have various shapes including, for example, granules, pellets, spheres, extrudates, and the like. The alumina catalyst may be disposed within a ketonization zone. A ketonization zone is not limited to any particular reactor type. For example, a ketonization zone may use a fixed-, fluidized-, or moving bed reactor.

Over time, the ketonization catalyst may passivate and lose activity. An alumina catalyst that has become passivated to varying degrees following ketonization may be regenerated, e.g., as described in commonly assigned U.S. patent application Ser. No. 14/540,723, filed on even date herewith and entitled Ketonization process using oxidative catalyst regeneration.

Fatty Acid Ketonization

A ketone product may be prepared by contacting at least one fatty acid with a ketonization catalyst in a ketonization zone under ketonization conditions according to the following scheme (Scheme 1), wherein $R_1$ and $R_2$ are saturated or unsaturated aliphatic groups, and wherein $R_1$ and $R_2$ may be the same or different. As a non-limiting example, $R_1$ and $R_2$ may be independently selected from $C_5$-$C_{21}$ linear or branched alkyl and $C_5$-$C_{21}$ linear or branched alkenyl.

Scheme 1:

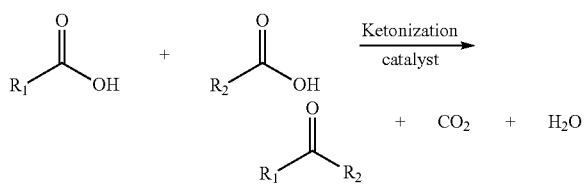

In a sub-embodiment, $R_1$ and $R_2$ may be independently selected from $C_7$-$C_{17}$ linear or branched alkyl or alkenyl, or from $C_9$-$C_{17}$ linear or branched alkyl or alkenyl, or from $C_9$-$C_{15}$ linear or branched alkyl or alkenyl, or from $C_{15}$-$C_{17}$ linear or branched alkyl or alkenyl. In an embodiment, ketonization may also be known as ketonic decarboxylation or fatty acid decarboxylation-coupling.

In an embodiment, the step of contacting the at least one fatty acid with the ketonization catalyst may comprise feeding a feedstock comprising the at least one fatty acid to the ketonization zone. In an embodiment, feedstocks for ketonization as disclosed herein may be derived from a triglyceride-containing biomass source such as oils or fats from plants and/or animals. In an embodiment, the feedstock may be obtained from biological material (e.g., fatty biomass) having a lipid content greater than (>) 30 wt % on a dry weight basis, or >50, or >70, or >90, or >95, or >99 wt % on a dry weight basis. In an embodiment, the biological material may comprises vegetable oil, animal tallow, algae, and combinations thereof. In an embodiment, the fatty acid feedstock may be derived from other, non-biomass, sources (e.g., Fischer-Tropsch synthesis). Such alternatively derived fatty acids may be mixed or blended with biomass derived fatty acids prior to ketonization, e.g., to alleviate logistical and/or supply related issues involving biomass.

In an embodiment, feedstocks for ketonization may comprise at least one fatty acid reactant or a mixture of fatty acid reactants. In an embodiment, the at least one fatty acid reactant for ketonization may comprise a mixture of at least two (2) fatty acids. In an embodiment, reactants for ketonization may comprise $C_6$-$C_{22}$ fatty acids and/or $C_6$-$C_{22}$ fatty acid derivatives. In an embodiment, such fatty acid derivatives may include $C_6$-$C_{22}$ fatty acid mono-, di-, and triglycerides, $C_6$-$C_{22}$ acyl halides, and $C_6$-$C_{22}$ salts of fatty acids. In a sub-embodiment, the fatty acids and/or fatty acid derivatives for ketonization may be in the range from $C_8$-$C_{18}$, or in the range from $C_{16}$-$C_{18}$. In an embodiment, at least one fatty acid for ketonization may be obtained from biological material, including various organisms and biological systems. In an embodiment, the at least one fatty acid may be obtained from at least one naturally occurring triglyceride, for example, wherein the triglyceride may be obtained from biomass. In an embodiment, feedstocks for ketonization may comprise at least 95 wt % fatty acids or at least 99 wt % fatty acids.

In an embodiment, reactants for ketonization may be derived from one or more triglyceride-containing vegetable oils such as, but not limited to, coconut oil, corn oil, linseed oil, olive oil, palm oil, palm kernel oil, rapeseed oil, safflower oil, soybean oil, sunflower oil, and the like. Additional or alternative sources of triglycerides, which can be hydrolyzed to yield fatty acids, include, but are not limited to, algae, animal tallow, and zooplankton.

In an embodiment, reactants for ketonization may include, without limitation, $C_8$-$C_{22}$ fatty acids, and combinations thereof. Examples of suitable saturated fatty acids may include, without limitation, caproic acid ($C_6$), caprylic acid ($C_8$), capric acid ($C_{10}$), lauric acid ($C_{12}$), myristic acid ($C_{14}$), palmitic acid ($C_{16}$), stearic acid ($C_{18}$), eicosanoic acid ($C_{20}$). Examples of unsaturated fatty acids may include, without limitation, palmitoleic acid, oleic acid, and linoleic acid. Reactants for ketonization may further include, without limitation, palm kernel oil, palm oil, coconut oil, corn oil, soy bean oil, rape seed (canola) oil, poultry fat, beef tallow, and their respective fatty acid constituents, and combinations thereof.

In an embodiment, the reactants for the ketonization reaction or step may be hydrogenated to substantially saturate some or all of the double bonds prior to ketonization. In cases where the fatty oils, i.e., triglycerides, are hydrolyzed to fatty acids, such saturation of the double bonds may be done before or after the hydrolysis.

In some aspects, wherein the above-mentioned hydrolyzed triglyceride sources contain mixtures of saturated fatty acids, mono-unsaturated fatty acids, and polyunsaturated fatty acids, one or more techniques may be employed to isolate, concentrate, or otherwise separate one or more types of fatty acids from one or more other types of fatty acids in the mixture (see, e.g., U.S. Pat. No. 8,097,740 to Miller).

Prior to contacting the reactant with the ketonization catalyst in the ketonization zone, the ketonization catalyst may be calcined. In an embodiment, the step of calcining the ketonization catalyst may be performed in the presence of steam. In an embodiment, the step of calcining the ketonization catalyst may be performed at a temperature in the range from 400 to 600° C., or from 450 to 500° C., for a time period in the range from 0.5 to 10 hours, or from 1 to 2 hours.

In an embodiment, a suitable catalyst for fatty acid ketonization may comprise alumina. In an embodiment, the ketonization catalyst may comprise substantially pure gamma alumina. In an embodiment, the ketonization catalyst may consist essentially of alumina. Suitable ketonization conditions may include a temperature in the range from 100 to 500° C., or from 300 to 450° C.; a pressure in the range from 0.5 to 100 psi, or from 5 to 30 psi; and a liquid hourly space velocity (LHSV) in the range from 0.1 to 50 h$^{-1}$, or from 0.5 to 10 h$^{-1}$. In an embodiment, the partial pressure of the fatty acid in the ketonization zone may be maintained in the range of 0.1 to 30 psi. The ketonization process can be carried out in batch or continuous mode, with recycling of unconsumed starting materials if required.

In an embodiment, the decarboxylation reaction may be conducted in the presence of at least one gaseous- or liquid feedstock diluent. In an embodiment, the ketonization reaction may be carried out while the fatty acid is maintained in the vapor phase. Conditions for fatty acid ketonization are disclosed in commonly assigned U.S. patent application Ser. No. 13/486,097, filed Jun. 1, 2012, entitled Process for producing ketones from fatty acids. In an embodiment, a fatty acid reactant for the ketonization reaction may comprises a mixture of at least two (2) fatty acids such that the ketone product may comprise a mixture of at least three (3) different long chain ketones, each of which may be selectively hydrogenated to provide a mixture of at least three (3) different long chain secondary alcohols.

In an embodiment, the long chain ketones provided by the ketonization reaction can be separated from by-products (such as oligomeric or polymeric species and low molecular weight "fragments" from the fatty acid chains) by distillation. For example, in an embodiment the crude reaction product can be subjected to a distillation-separation at atmospheric or reduced pressure through a packed distillation column. In an embodiment, the ketonization product may be a wax under ambient conditions.

The long chain ketones produced from fatty acids, e.g., as disclosed hereinabove, may be converted to their corresponding long chain secondary alcohol by selective ketone hydrogenation over a selective ketone hydrogenation catalyst, e.g., as disclosed hereinbelow.

Catalysts for Selective Ketone Hydrogenation

A catalyst for the selective hydrogenation of long chain ketones to the corresponding secondary alcohols may be referred to herein as a "selective ketone hydrogenation catalyst." In an embodiment, the selective ketone hydrogenation catalyst for selective hydrogenation of long chain (e.g., $C_{11}+$) ketones may comprise a metal selected from Pt, Pd, Ru, Ni, Co, Mo, Cr, Cu, Rh, and combinations thereof. In an embodiment, the selective ketone hydrogenation catalyst may further comprise a support material. In an embodiment, the support material may be selected from carbon, silica, magnesia, titania, and combinations thereof. In an embodiment, at least some metal component(s) of the hydrogenation catalyst may be in elemental form. As a non-limiting example, the hydrogenation catalyst may comprise a metal selected from Pt, Pd, Ru, Ni, Rh, and combinations thereof, and the metal may be in elemental form in the hydrogenation catalyst. In a sub-embodiment, the hydrogenation catalyst may comprise a metal selected from Pt, Pd, and combinations thereof, and a support material comprising carbon, silica, magnesia, titania, and combinations thereof. In an embodiment, the hydrogenation catalyst may be unsupported meaning, for example, that the metal may be present either in finely divided form (e.g., as metal powder) or in pelletized or extruded or other structural form without the presence of a support material.

In an embodiment, the selective ketone hydrogenation catalyst lacks, or is devoid of, any component that promotes the dehydration of alcohols, such that the hydrogenation catalyst as a whole lacks catalytic activity for dehydration of the long chain secondary alcohol, under the conditions used for the selective hydrogenation of long chain ketones, such that ketone conversion to the corresponding alkene or alkane is prevented. Because the long chain ketones as disclosed herein exhibit comparatively low reactivity in the ketone hydrogenation reaction, e.g., in comparison with $C_3$ or $C_4$ ketones, more forcing conditions may be required for hydrogenation as compared to hydrogenation of lighter ketones; such (more forcing) conditions would be expected to exacerbate the negative effect on product selectivity of a hydrogenation catalyst having dehydration functionality. This highlights the significance of using a selective ketone hydrogenation catalyst, in processes as disclosed herein, for the efficient conversion of long chain ketones to the corresponding long chain secondary alcohols in high yield.

In an embodiment, a selective ketone hydrogenation catalyst will lack alumina. As an example, the selective ketone hydrogenation catalyst may be prepared without the use of an alumina component and with a support material, if any, lacking an alumina component, such that the selective ketone hydrogenation catalyst contains at most only trace amounts of alumina that are insufficient to be catalytically effective in dehydrating long chain secondary alcohols under the hydrogenation conditions as disclosed herein for the selective hydrogenation of long chain ketones to the corresponding secondary alcohols.

This is in stark contrast to conventional hydrotreating catalysts having alumina support material that is the major catalyst component by weight and volume. Applicant has observed that the presence of alumina, e.g., in conventional hydrotreating catalysts, negatively impacts the conversion of long chain ketones to the corresponding secondary alcohol product(s) as disclosed herein.

In an embodiment, the surface area of the hydrogenation catalyst may be in the range from 15 to 1000 $m^2/g$ of catalyst, or from 100 to 600 $m^2/g$ of catalyst, or from 250 to 450 $m^2/g$ of catalyst. In an embodiment a selective ketone hydrogenation catalyst, useful for selective hydrogenation of long chain ketones as disclosed herein, may have various shapes including, for example, powder, granules, pellets, spheres, extrudates, and the like. The selective ketone hydrogenation catalyst may be disposed within a ketone hydrogenation zone or ketone hydrogenation reactor. The ketone hydrogenation zone is not limited to any particular reactor type.

Long Chain Secondary Alcohols by Selective Hydrogenation of Long Chain Ketones

As described hereinabove, a long chain ketone may be prepared, e.g., according to Scheme 1 by contacting at least one fatty acid with a ketonization catalyst in a ketonization zone under ketonization conditions. The long chain ketone may then be selectively hydrogenated by contacting the long chain ketone with a selective ketone hydrogenation catalyst in a ketone hydrogenation zone under selective ketone hydrogenation conditions according to the following Scheme 2 to provide a long chain secondary alcohol.

Scheme 2:

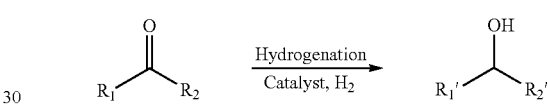

In Schemes 1 and 2, $R_1$ and $R_2$ may be the same or different, $R_1$ and $R_2$ may be independently selected from $C_5$-$C_{21}$ linear or branched alkyl and $C_5$-$C_{21}$ linear or branched alkenyl, wherein: when $R_1$ is alkyl $R_1'=R_1$, when $R_2$ is alkyl $R_2'=R_2$, when $R_1$ is alkenyl $R_1'$ is alkyl or alkenyl, when $R_2$ is alkenyl $R_2'$ is alkyl or alkenyl, and wherein $R_1$ and $R_1'$ have an equal number of carbon atoms, and $R_2$ and $R_2'$ have an equal number of carbon atoms. In an embodiment, $R_1'$ and $R_2'$ may be independently selected from $C_5$-$C_{21}$ linear or branched alkyl, or from $C_7$-$C_{17}$ linear or branched alkyl, or from $C_9$-$C_{17}$ linear or branched alkyl, or from $C_9$-$C_{15}$ linear or branched alkyl, or from $C_{15}$-$C_{17}$ linear or branched alkyl.

While not being bound by theory, in an embodiment wherein $R_1$ and $R_2$ are alkenyl, the product alcohol may be the corresponding saturated alcohol, since alkenyl group hydrogenation is typically more facile than ketone hydrogenation. As an example, when $R_1$ is alkenyl $R_1'$ may be alkyl, and when $R_2$ is alkenyl $R_2'$ may be alkyl.

In an embodiment, the at least one fatty acid may comprise a mixture of at least two (2) fatty acids, such that the long chain ketone prepared according to Scheme 1 may comprise a mixture of at least three (3) different long chain ketones, and the long chain secondary alcohol prepared according to Scheme 2 may similarly comprise a mixture of at least three (3) different long chain secondary alcohols.

In an embodiment, the selective ketone hydrogenation catalyst will lack catalytic activity for dehydration of the long chain secondary alcohol under the selective ketone hydrogenation conditions used such that, during the step of contacting the long chain ketone with the selective ketone hydrogenation catalyst, ketone conversion to the corresponding alkene or alkane is prevented or hindered. As a result, the corresponding secondary alcohol may be obtained from the long chain ketone with excellent selectivity (e.g., >80% selectivity at 90% conversion).

In an embodiment, a process for preparing long chain secondary alcohols may comprise avoiding contact of the at least one long chain ketone with alumina during the selective ketone hydrogenation step. For example, alumina promotes alcohol dehydration to alkenes, which may in turn be converted to alkanes during conventional hydrogenation, thereby substantially or greatly decreasing the yield of long chain secondary alcohols. Accordingly in an embodiment, the selective ketone hydrogenation catalyst as disclosed herein may be prepared without the use of alumina. In an embodiment, alumina or other material(s) that promote(s) alcohol dehydration may be specifically excluded from the selective ketone hydrogenation catalyst and the ketone hydrogenation zone.

In an embodiment, the selective ketone hydrogenation catalyst may comprise a metal selected from Pt, Pd, Ru, Ni, Co, Mo, Cr, Cu, Rh, and combinations thereof. In an embodiment, the hydrogenation catalyst may further comprise a support material selected from carbon, silica, magnesia, titania, and combinations thereof. In a sub-embodiment, the hydrogenation catalyst may comprise a metal selected from the group consisting of Pt, Pd, and combinations thereof, and a support material selected from carbon, silica, magnesia, titania, and combinations thereof.

In an embodiment, the ketone hydrogenation step may be performed in the absence of a material that promotes dehydration of the long chain secondary alcohol under the selective ketone hydrogenation conditions used, so as to prevent or hinder ketone conversion to the corresponding alkene or alkane, in order to greatly increase the selectivity of ketone conversion to the long chain secondary alcohol product. As a non-limiting example, the selective ketone hydrogenation step may be performed in the absence of alumina. Alumina is used as a catalyst support in conventional hydrotreating catalysts; however, processes as disclosed herein may involve avoiding the presence of alumina during ketone hydrogenation for the production of long chain secondary alcohols. In an embodiment, alumina may be avoided during the ketone hydrogenation step by using a selective ketone hydrogenation catalyst that lacks an alumina component. Selective ketone hydrogenation catalysts that lack alumina are described hereinabove.

In an embodiment, the selectivity of long chain ketone conversion to the corresponding long chain secondary alcohol via the selective ketone hydrogenation step (e.g., according to Scheme 2) may be much higher, e.g., typically at least about 15% higher, than that of comparable ketone hydrogenation in the presence of a conventional hydrotreating catalyst comprising alumina. As a non-limiting example, the selectivity of ketone conversion to the corresponding long chain secondary alcohol by a selective ketone hydrogenation catalyst as disclosed herein may be greater than (>) 80% at 90% conversion, whereas the selectivity of ketone conversion to the corresponding long chain secondary alcohol by a conventional hydrogenation catalyst comprising an alumina support is typically less than (<) 70% at 90% conversion.

In an embodiment, $R_1$ and $R_2$ in Schemes 1 and 2 may each be linear or branched alkyl. In a sub-embodiment, $R_1$ and $R_2$ may be independently selected from $C_5$-$C_{21}$ linear or branched alkyl, or from $C_7$-$C_{17}$ linear or branched alkyl, or from $C_9$-$C_{17}$ linear or branched alkyl, or from $C_9$-$C_{15}$ linear or branched alkyl, or from $C_{15}$-$C_{17}$ linear or branched alkyl. In an embodiment, the at least one long chain secondary alcohol formed by ketone hydrogenation, e.g., according to Scheme 2, may be in the range from $C_{11}$-$C_{43}$, or from $C_{21}$-$C_{31}$, or from $C_{31}$-$C_{35}$. In an embodiment, long chain secondary alcohols prepared by processes as disclosed herein may comprise a mixture of long chain secondary alcohols, e.g., each having from 11 to 43 carbon atoms per molecule. In an embodiment, each of the long chain secondary alcohols may have the hydroxyl group placed at a non-terminal location of the molecule. In a further embodiment, a long chain secondary alcohol prepared according to embodiments of processes disclosed herein may have the OH group placed at—or near the center of the secondary alcohol molecule.

In an embodiment, fatty acid ketonization may comprise contacting a mixture of at least two (2) fatty acids with the ketonization catalyst in the ketonization zone. In an embodiment, such a mixture of fatty acids may comprise a lipid mixture derived from a source of lipids selected from a plant, an animal, or other organism(s). Such sources of lipids may include, without limitation, terrestrial plants, mammals, microorganisms, aquatic plants, seaweed, algae, phytoplankton, and the like. In an embodiment, a mixture of fatty acids for ketonization according to processes as disclosed herein may be derived from palm kernel oil, palm oil, coconut oil, corn oil, soy bean oil, rape seed (canola) oil, poultry fat, beef tallow, and the like and their respective fatty acid constituents, and combinations thereof.

In another embodiment, a process for preparing a long chain secondary alcohol may comprise reacting a first fatty acid with a second fatty acid to form a long chain ketone, and selectively hydrogenating the long chain ketone to selectively form the corresponding secondary alcohol. In an embodiment, the reacting step and the ketone hydrogenating step may be jointly performed according to the following Scheme 3.

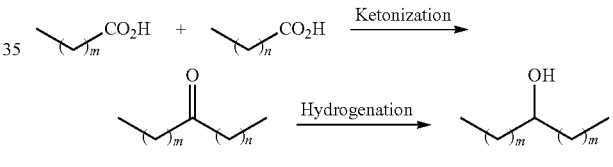

Scheme 3 combines or summarizes the reactions of Schemes 1 and 2 (supra) for embodiments wherein the fatty acid reactants for ketonization are saturated. In an embodiment, each of m and n is an integer in the range from 4 to 20, or from 8 to 16, or from 8 to 14, or from 14 to 16; wherein m and n may be equal or unequal such that the first fatty acid and the second fatty acid may be the same or different. In an embodiment, the reacting step may comprise contacting the first fatty acid and the second fatty acid with a ketonization catalyst in a ketonization zone under ketonization conditions.

In an embodiment, the selectively hydrogenating step may comprise contacting the long chain ketone with a selective ketone hydrogenation catalyst in a ketone hydrogenation zone under selective ketone hydrogenation conditions. In an embodiment, the selective ketone hydrogenation catalyst will lack catalytic activity for dehydration of the secondary alcohol, under the selective ketone hydrogenation conditions used, such that ketone conversion to the corresponding alkene or alkane is prevented. Due to the relatively low reactivity of long chain ketones (e.g., $C_{11}$-$C_{43}$) in the ketone hydrogenation reaction, as compared with lighter ketones (e.g., $C_3$ or $C_4$), the more forcing conditions used for the long chain ketones would exacerbate the negative effect that a hydrogenation catalyst having dehydration functionality would have on product selectivity. Instead, the use of a selective ketone hydrogenation catalyst that at least substantially lacks dehydration activity, as disclosed herein, allows for the efficient conversion of long chain ketones with high selectivity to the corresponding long chain secondary alcohols.

In an embodiment, exemplary conditions for selective ketone hydrogenation may comprise a temperature in the range from 200 to 755° F. (93 to 402° C.), or from 355 to 755° F. (179 to 402° C.), or from 400 to 750° F. (204 to 399° C.), a pressure in the range from 200 to 5000 psi, or from 250 to 5000 psi, or from 300 to 4000 psi, a liquid hourly space velocity (LHSV) in the range from 0.05 to 5.0 h$^{-1}$, or from 0.1 to 5.0 h$^{-1}$, or from 0.5 to 4.0 h$^{-1}$, and a hydrogen to feed molar ratio in the range from 1.0 to 1000, or from 5.0 to 1000, or from 10 to 1000. In an embodiment, the hydrogenation catalyst may comprise a metal selected from the group consisting of Pt, Pd, Ru, Ni, Co, Mo, Cr, Cu, Rh, and combinations thereof. In a sub-embodiment, the metal may be selected from Pt, Pd, and combinations thereof.

As described hereinabove, the selective hydrogenation of long chain ketones may be performed in the absence of a material that promotes dehydration of the secondary alcohol under selective ketone hydrogenation conditions, such that conversion to the corresponding alkene or alkane is prevented or hindered. Accordingly, the selective ketone hydrogenation catalyst will lack a material, such as alumina, that promotes dehydration of the secondary alcohol under said selective ketone hydrogenation conditions. This is in contrast to conventional hydrotreating catalysts having an alumina support that promotes alcohol dehydration to alkenes, with subsequent hydrogenation to alkanes. Advantageously, selective ketone hydrogenation as disclosed herein allows the corresponding secondary alcohol to be obtained efficiently with excellent selectivity.

In an embodiment, long chain secondary alcohol product(s) prepared as disclosed herein may comprise a mixture of long chain secondary alcohols and may be subjected to various separation processes. Such separation may involve, for example, distilling and/or flash distillation to provide one or more long chain secondary alcohol products.

Distilling

In an embodiment, a step of distilling may employ one or more distillation columns to separate the desired product(s) from by-products. In an embodiment, the step of distilling may employ flash distillation or partial condensation techniques to remove by-products including at least low molecular weight materials. Those of skill in the art will recognize that there is some flexibility in characterizing the high and low boiling fractions, and that the products may be obtained from "cuts" at various temperature ranges.

EXAMPLES

Example 1

Ketonization of Lauric Acid to Laurone Using Alumina Catalyst

The ketonization of lauric acid to 12-tricosanone (laurone) was catalyzed by an alumina catalyst operated in a fixed bed continuously fed reactor at ambient pressure, at a temperature range of 770-840° C., and with a feed rate that gave a liquid hourly space velocity (LHSV) of 0.62-0.64 h$^{-1}$. The conversion rate of lauric acid to laurone was calculated based on the composition of the product as determined by GC analysis using an FID detector.

The freshly loaded new alumina catalyst was calcined in the reactor at 900° F. (482° C.) with a stream of dry nitrogen (2 volumes of nitrogen per volume of catalyst per minute) for 2 hours before the temperature was lowered to 770° F. (410° C.), nitrogen was turned off and the lauric acid feed was introduced. Product composition analysis showed that the fresh catalyst operating at 770° F., LHSV=0.62-0.64 h$^{-1}$, gave a lauric acid conversion of 62-66%.

Example 2

Hydrogenation of 12-tricosanone to 12-tricosanol over a Pt/Carbon hydrogenation catalyst 12-tricosanone (laurone) prepared by ketonization reaction of lauric acid over alumina catalyst was hydrogenated over a carbon supported platinum catalyst to make the corresponding alcohol, 12-tricosanol.

12-tricosanone was introduced as a liquid flow (4.1-4.4 g/hr, 12-13 mmoles/hr) together with hydrogen (100 Nml/min, 250 mmoles/hr) to a fixed reactor holding 7 ml of 0.5% Pt/carbon (3.5 g, particle size: 0.3-1 mm). The pressure was held at 1500 psi. The liquid products were collected after the reaction and analyzed by GC. The liquid product stream was found to contain three components: unconverted 12-tricosanone and two products: the target alcohol, 12-tricosanol, and the corresponding n-alkane, n-tricosane, of which the latter was present only in trace amounts.

At 450-470° F. reaction temperature the GC analysis of the product showed a conversion of 12-tricosanone of 80-87% and a selectivity to 12-tricosanol of 98.9-99.4% with the remaining 0.6-1.1% being n-tricosane formed by hydrodeoxygenation of the alcohol.

Example 3

Hydrogenation of Coconut Fatty Acid Derived Ketones to a Mixture of Linear Secondary Alcohols Saturated fatty acids from coconut oil contain a mixture of $C_8$-$C_{14}$ fatty acids with $C_{12}$ and $C_{14}$ fatty acids being the predominant components. Such a coconut fatty oil-derived mixture of fatty acids were reacted under ketonization conditions over alumina catalyst at 790-820° F. and atmospheric pressure to prepare a product mixture from which a mixture of $C_{19}$-$C_{27}$ ketones with >90% ketones and less than 1% unconverted fatty acids were isolated.

The above mentioned coconut-derived ketone mixture was converted to the corresponding alcohols by hydrogenation over a fixed bed of 0.5% Pt/carbon catalyst. Hydrogenation at 1500 psi pressure and 450-460° F. gave about 90% ketone conversion to a mixture of the corresponding alcohols (80-90% selectivity) and the corresponding alkanes (10-20% selectivity) based on GC analysis of the mixed products. We expect that improved selectivity is achievable through optimization of the reactor and flow distribution.

Example 4

$C_{29}$-$C_{35}$ Linear Alcohols from Beef Tallow Fatty Acids

A saturated fatty acid mixture (Product TRT1655 from Twin Rivers Technologies, Quincy, Mass.) prepared from beef tallow and consisting predominantly of stearic acid (octadecanoic acid, about 45%) and palmitic acid (hexadecanoic acid, about 45%) with smaller amounts of myristic acid (tetradecanoic acid, about 5%) and other fatty acids was processed over an alumina catalyst at 800-810° F. and atmospheric pressure to produce a reactor effluent from which a product mixture of predominantly $C_{29}$-$C_{35}$ ketones with less than 0.15 wt % fatty acids were isolated.

This beef tallow-derived ketone mixture was hydrogenated over a 0.5% Pt/carbon catalyst at 650° F. and 1588 psi hydrogen at a LHSV=0.48 h$^{-1}$ to yield the corresponding $C_{29}$-$C_{35}$ secondary alcohol mixture with a ketone conversion of about 82% and a selectivity above 99%.

Long chain secondary alcohols prepared from inexpensive feedstocks according to processes as disclosed herein may be converted to a range of valuable products including lubricants.

Example 5

Comparative: Hydrogenation of Laurone Over Alumina Supported Cobalt-Molybdenum Catalyst 6 ml of an alumina supported cobalt-molybdenum catalyst was loaded into a fixed bed reactor in its oxide form and activated as follows. First the catalyst was dried by slow heating to 450° F. where the temperature was held for 1 hr. (heating rate: 100° F./hr, nitrogen flow: 500 Nml/min, 100 psi). After 1 hr of nitrogen treatment at 450° F. hydrogen was passed over the catalyst at a rate of 500 Nml/min at 100 psi, 450° F. After 1 hr of hydrogen treatment the pressure was increased to 800 psi and the catalyst was sulfided by treatment with dimethyl disulfide solution in heptane. This treatment was initially done at 450° F., then gradually at increasing temperature to 650° F. and then at the latter temperature for a couple of hours to ensure complete sulfidation.

The sulfided catalyst was cooled to 300° F., laurone (12-tricosanone) was introduced at a flow of 15 g/hr and subsequently the temperature was adjusted to reaction conditions.

At 350° F., 1000 psi and 300 Nml/min hydrogen the ketone conversion was found to be less than 25%.

The laurone feed flow was lowered to 8 g/hr, hydrogen flow lowered to 150 Nml/min, the pressure raised to 1750 psi and the temperature raised to 400° F. At these conditions the conversion was 92% but the selectivity to tricosanol was only 62%, the remainder of the product being tricosane. Lowering the temperature to 385° F. improved the selectivity (82% selectivity to tricosanol) but the ketone conversion was now only 58%.

It was concluded from the results in comparative Example 5 that, although we used a particularly active hydrogenation catalyst and thus were able to hydrogenate the ketone at relatively low temperature, the alumina support (a known dehydration catalyst) still dehydrated sufficient of the alcohol to make unacceptably large amounts of the alkane even at fairly low conversion. Conceivably, a cobalt-molybdenum catalyst on a different support may have better selectivity but this was not tested.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Additionally, chemical species including reactants and products designated by a numerical range of carbon atoms include any one or more of, or any combination of, or all of the chemical species within that range.

Any term, abbreviation or shorthand not defined is understood to have the ordinary meaning used by a person skilled in the art at the time the application is filed. The singular forms "a," "an," and "the," include plural references unless expressly and unequivocally limited to one instance. All publications, patents, and patent applications cited in this application are incorporated by reference herein in their entirety to the extent not inconsistent herewith.

Modifications of the exemplary embodiments disclosed above may be apparent to those skilled in the art in light of this disclosure. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible sub-generic combinations of the listed components and mixtures thereof.

What is claimed is:

1. A process comprising:
   a) contacting at least one fatty acid with a ketonization catalyst in a ketonization zone under ketonization conditions to provide at least one long chain ketone according to the following Scheme 1:

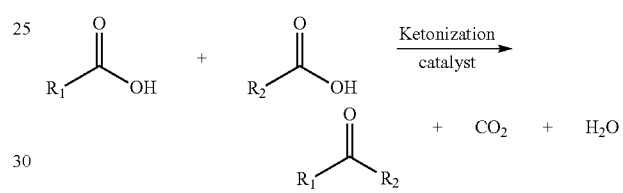

wherein $R_1$ and $R_2$ are independently selected from the group consisting of $C_5$-$C_{21}$ linear or branched alkyl and $C_5$-$C_{21}$ linear or branched alkenyl, and b) contacting the at least one long chain ketone with a selective ketone hydrogenation catalyst in a ketone hydrogenation zone in the presence of hydrogen gas under selective ketone hydrogenation conditions to provide at least one long chain secondary alcohol according to the following Scheme 2:

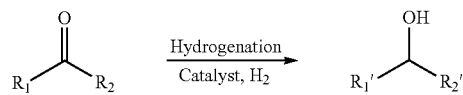

wherein:
$R_1$ and $R_2$ are the same or different,
when $R_1$ is alkyl $R_1'$=$R_1$,
when $R_2$ is alkyl $R_2'$=$R_2$,
when $R_1$ is alkenyl $R_1'$ is alkyl or alkenyl,
when $R_2$ is alkenyl $R_2'$ is alkyl or alkenyl,
$R_1$ and $R_1'$ have an equal number of carbon atoms,
$R_2$ and $R_2'$ have an equal number of carbon atoms, and
step b) comprises selectively hydrogenating the at least one long chain ketone to selectively provide the at least one long chain secondary alcohol.

2. The process according to claim 1, wherein step b) is performed in the absence of a material that promotes dehydration of the long chain secondary alcohol under said selective ketone hydrogenation conditions so as to prevent ketone conversion to the corresponding alkene or alkane.

3. The process according to claim 1, wherein the selective ketone hydrogenation catalyst lacks catalytic activity for dehydration of the long chain secondary alcohol under said selective ketone hydrogenation conditions such that ketone conversion to the corresponding alkene or alkane is prevented.

4. The process according to claim 1, wherein:
the ketonization catalyst consists essentially of alumina, and the process further comprises:
c) avoiding the presence of alumina during step b).

5. The process according to claim 1, wherein the at least one long chain secondary alcohol is in the range from $C_{19}$-$C_{43}$.

6. The process according to claim 1, wherein the selective ketone hydrogenation catalyst comprises a metal selected from the group consisting of Pt, Pd, Ru, Ni, Co, Mo, Cr, Cu, Rh, and combinations thereof.

7. The process according to claim 6, wherein the selective ketone hydrogenation catalyst further comprises a support material selected from the group consisting of carbon, silica, magnesia, titania, and combinations thereof.

8. The process according to claim 1, wherein the selective ketone hydrogenation catalyst comprises:
a metal selected from the group consisting of Pt, Pd, and combinations thereof, and
a support material selected from the group consisting of carbon, silica, magnesia, titania, and combinations thereof.

9. The process according to claim 1, wherein:
the selective ketone hydrogenation catalyst comprises a metal selected from the group consisting of Pt, Pd, Ru, Ni, Rh, and combinations thereof, and the metal is in elemental form.

10. The process according to claim 1, wherein step b) comprises selectively hydrogenating the at least one long chain ketone such that the selectivity of ketone conversion to the corresponding long chain secondary alcohol is greater than 80% at 90% conversion.

11. The process according to claim 1, wherein said selective ketone hydrogenation conditions comprise a temperature in the range from 200 to 755° F., a pressure in the range from 200 to 5000 psi, a LHSV in the range from 0.05 to 5.0 hr$^{-1}$, and a hydrogen to feed molar ratio in the range from 1.0 to 1000.

12. The process according to claim 1, wherein: when $R_1$ is alkenyl $R_1'$ is alkyl, and when $R_2$ is alkenyl $R_2'$ is alkyl.

13. The process according to claim 1, wherein $R_1'$ and $R_2'$ are independently selected from the group consisting of linear or branched $C_7$-$C_{17}$ alkyl.

14. The process according to claim 1, wherein:
the at least one fatty acid comprises a mixture of at least two (2) fatty acids,
the at least one long chain ketone comprises a mixture of at least three (3) ketones, and
the at least one long chain secondary alcohol comprises a mixture of at least three (3) long chain secondary alcohols.

15. The process according to claim 1, wherein:
step a) comprises feeding a feedstock comprising the at least one fatty acid to the ketonization zone, and
the feedstock is obtained from biological material having a lipid content of at least 30 wt % on a dry weight basis.

16. A process comprising:
a) contacting at least one fatty acid with a ketonization catalyst in a ketonization zone under ketonization conditions to provide at least one long chain ketone having at least 11 carbon atoms according to the following Scheme 1:

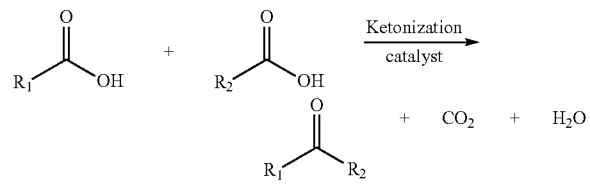

wherein $R_1$ and $R_2$ are independently selected from the group consisting of $C_5$-$C_{21}$ linear or branched alkyl and $C_5$-$C_{21}$ linear or branched alkenyl, and b) contacting the at least one long chain ketone with a selective ketone hydrogenation catalyst in a ketone hydrogenation zone in the presence of hydrogen gas under selective ketone hydrogenation conditions to provide at least one long chain secondary alcohol according to the following Scheme 2:

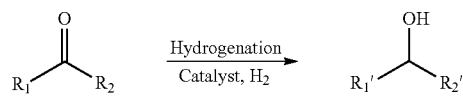

wherein:
$R_1$ and $R_2$ are the same or different,
when $R_1$ is alkyl $R_1'$=$R_1$,
when $R_2$ is alkyl $R_2'$=$R_2$,
when $R_1$ is alkenyl $R_1'$ is alkyl or alkenyl,
when $R_2$ is alkenyl $R_2'$ is alkyl or alkenyl,
$R_1$ and $R_1'$ have an equal number of carbon atoms,
$R_2$ and $R_2'$ have an equal number of carbon atoms,
the selective ketone hydrogenation catalyst lacks catalytic activity for dehydration of the long chain secondary alcohol under said selective ketone hydrogenation conditions such that ketone conversion to the corresponding alkene or alkane is prevented, and
step b) comprises selectively hydrogenating the at least one ketone to selectively provide the at least one long chain secondary alcohol.

17. The process according to claim 16, wherein:
the ketonization catalyst consists essentially of alumina,
the selective ketone hydrogenation catalyst comprises a metal and a support material,
the metal is selected from the group consisting of Pt, Pd, Ru, Ni, Cr, Cu, Rh, and combinations thereof,
the support material is selected from the group consisting of carbon, silica, magnesia, titania, and combinations thereof, and
step b) is performed in the absence of alumina.

18. A process comprising:
a) reacting a first fatty acid with a second fatty acid to form a long chain ketone having at least 11 carbon atoms; and
b) selectively hydrogenating the long chain ketone to selectively form the corresponding long chain secondary alcohol, wherein steps a) and b) are jointly performed according to the following Scheme 3:

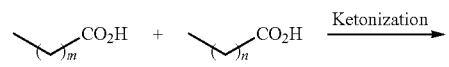

-continued

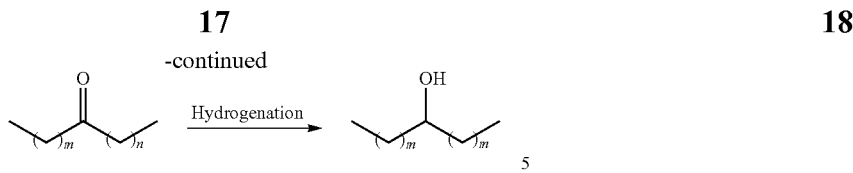

wherein:
    each of m and n is an integer in the range from 4 to 20, wherein m and n may be equal or unequal such that the first fatty acid and the second fatty acid may be the same or different,
    step a) comprises contacting the first fatty acid and the second fatty acid with a ketonization catalyst in a ketonization zone under ketonization conditions,
    step b) comprises contacting the long chain ketone with a selective ketone hydrogenation catalyst in a ketone hydrogenation zone in the presence of hydrogen gas under selective ketone hydrogenation conditions, and
    step b) is performed in the absence of a material that promotes dehydration of the secondary alcohol under said selective ketone hydrogenation conditions such that ketone conversion to the corresponding alkene or alkane is prevented.

19. The process according to claim 18, wherein:
    the selective ketone hydrogenation catalyst comprises a metal selected from the group consisting of Pt, Pd, Ru, Ni, Co, Mo, Cr, Cu, Rh, and combinations thereof, and
    the selective ketone hydrogenation catalyst further comprises a support material selected from the group consisting of carbon, silica, magnesia, titania, and combinations thereof.

* * * * *